United States Patent
Girault et al.

[11] Patent Number: 5,635,054
[45] Date of Patent: Jun. 3, 1997

[54] MICROELECTRODES AND AMPEROMETRIC ASSAYS

[75] Inventors: Hubert H. J. Girault, Edinburgh; Brian J. Seddon, St. Helens, both of United Kingdom

[73] Assignee: Ecossensors Limited, Edinburgh, United Kingdom

[21] Appl. No.: 399,176

[22] Filed: Mar. 6, 1995

Related U.S. Application Data

[63] Continuation of Ser. No. 852,223, filed as PCT/GB90/01874 Dec. 3, 1990, Pat. No. 5,512,489.

[30] Foreign Application Priority Data

Dec. 4, 1989 [GB] United Kingdom ............... 8927377
Dec. 3, 1990 [WO] WIPO ............... PCT/GB90/01874

[51] Int. Cl.⁶ ............................................. G01N 27/26
[52] U.S. Cl. ............... 205/775; 205/790; 204/412; 204/413; 204/434; 436/73; 436/74; 436/75
[58] Field of Search ............... 436/73, 74, 75; 204/412, 413, 434, 153.1; 205/775, 781.5, 790

[56] References Cited

U.S. PATENT DOCUMENTS

| | | | |
|---|---|---|---|
| 3,854,193 | 12/1974 | Yamaguchi et al. | 29/473.9 |
| 3,855,099 | 12/1974 | Matson | 204/195 F |
| 3,904,487 | 9/1975 | Liberman | 204/1 T |
| 3,914,509 | 10/1975 | Tennent | 428/408 |
| 4,003,705 | 1/1977 | Buzza et al. | 23/230 R |
| 4,062,750 | 12/1977 | Butler | 104/195 P |
| 4,090,926 | 5/1978 | Matson | 204/1 T |
| 4,115,209 | 9/1978 | Fresier et al. | 204/1 T |
| 4,214,968 | 7/1980 | Battaglia et al. | 204/195 M |
| 4,233,031 | 11/1980 | Matson et al. | 23/230 B |
| 4,450,842 | 5/1984 | Zick et al. | 128/635 |
| 4,545,382 | 10/1985 | Higgins et al. | 128/635 |
| 4,661,210 | 4/1987 | Tenygl | 204/409 |
| 4,695,555 | 9/1987 | O'Keeffe | 436/150 |
| 4,786,373 | 11/1988 | Saloheimo et al. | 204/434 |
| 4,804,443 | 2/1989 | Newman et al. | 204/406 |
| 4,865,992 | 9/1989 | Hach et al. | 436/51 |
| 5,019,515 | 5/1991 | Gisin et al. | 436/52 |
| 5,120,421 | 6/1992 | Glass et al. | 204/415 |
| 5,131,999 | 7/1992 | Gunasingham | 204/411 |
| 5,192,416 | 3/1993 | Wang et al. | 204/409 |
| 5,290,420 | 3/1994 | Matson | 204/403 |
| 5,292,423 | 3/1994 | Wang | 204/434 |

FOREIGN PATENT DOCUMENTS

| | | |
|---|---|---|
| 0255291 | 2/1988 | European Pat. Off. . |
| 0286753 | 10/1988 | European Pat. Off. . |
| 0470649 | 2/1992 | European Pat. Off. . |
| 0529155A1 | 3/1993 | European Pat. Off. . |
| 0560137A1 | 9/1993 | European Pat. Off. . |
| 2451659 | 11/1973 | Germany . |
| 1382873 | 2/1975 | United Kingdom . |
| 1395425 | 5/1975 | United Kingdom . |
| 1600146 | 10/1981 | United Kingdom . |
| WO89/04479 | 5/1989 | WIPO . |
| WO89/09388 | 10/1989 | WIPO . |
| WO92/18857 | 10/1992 | WIPO . |
| WO92/21961 | 12/1992 | WIPO . |
| WO94/10558 | 5/1994 | WIPO . |
| WO94/28405 | 12/1994 | WIPO . |
| WO95/04271 | 2/1995 | WIPO . |

OTHER PUBLICATIONS

J. Electroanal Chem. 12 (1966) 269–276, S.P. Perrone and K.K. Davenport.

Steward, "Flow Injection Analysis–New Tool for Old Assays–New Approach to Analytical Measurements" *Analytical Chemistry*, vol. 55, No. 9 (Aug. 1983).

(List continued on next page.)

*Primary Examiner*—Bruce F. Bell
*Attorney, Agent, or Firm*—Darby & Darby

[57] ABSTRACT

A photo-ablation technique is used to create apertures (4) in a layer (2) of electrically insulating material and allow electrically conducting material (3) exposed through the apertures to create a microelectrode. The microelectrode can be used for assay methods and in an assay unit.

128 Claims, 3 Drawing Sheets

OTHER PUBLICATIONS

Wang, "Anodic Stripping Voltammetry as an Analytical Tool" *Environ. Sci. Technol.*, vol. 16, No. 2 (1982).

Hilditch, "Disposable Electrochemical Biosensors" *Analyst*, vol. 116 (Dec. 1991).

Oakton® ElectraScan®, EC-1 Series sales brochure (Feb. 1991).

Wang, "Anodic Stripping Voltammetry–An Instrumental Analysis Experiment" *Chem. Education*, vol. 60, p. 1074 (Dec. 1983).

Green, "Disposable Single–Use Sensors" *Analytical Proc.*, vol. 28 (Nov. 1991).

Wang, "Mercury=Coated Carbon–Foam Composite Electrodes for Stripping Analysis of Trace Metals" *Amer. Chem. Soc.*, vol. 64, (1992).

Wang, "Stripping Analysis–Principles, Instrumentation, and Applications", VCH Publishers, Inc., Deerfield Beach, Florida (1985).

MICROELECTRODES AND AMPEROMETRIC ASSAYS

This is a continuation of application Ser. No. 07/852,223, filed as PCT/GB90/01874 Dec. 3, 1990, now U.S. Pat. No. 5,512,489.

TECHNICAL FIELD

This invention relates to an improved method of making an electrode (in particular a microelectrode), an electrode made by the method, an assay method for the determination of the presence of a redox species (e.g. a heavy metal) in liquid carrier media using the electrode and redox species detection equipment designed to utilize she assay method.

BACKGROUND ART

Microelectrodes provide many advantages in electro-chemistry and electroanalysis (some of which are discussed in Wightman, R. M., Anal. Chem., 1982, 54, 2532) in particular the possibility of electrolysis in resistive media or dilute solutions, and of microanalysis with improved sensitivity and precision. For these reasons a great deal of effort has been dedicated to establish a way of fabricating a regular microscopic disc array electrode. Any proposed method of fabrication must ensure that all the distinctive features of individual microelectrodes are retained, and in addition circumvent the problems associated with the measurement of extremely small currents (pA-nA), observed for single microdisc electrodes.

Many approaches have been proposed for the construction of a microdisc array electrode including photolithographic methods (see e.g. Osteryoung, J. and Hempel, T., J. Electrochem. Soc., 1986. 133, 757–760 and W. Siu and R. S. C. Cobbold, Med. & Biol. Eng., 1976, 14, 109), as well as the use of micropore membrane matrices (see e.g. Wang, J., J. Electrochem. Soc., 1988, 249, 339–345, and Cheng, F., Anal. Chem., 1989, 61, 762–766). The former approach failed because of adhesion problems between the insulating photoresist layer and the metal substrate. The latter method of fabrication was self defeating because, although the size of the more is well characterized, the pore density and distribution were undefined and the electrode ultimately irreproducible.

SUMMARY OF THE INVENTION

According to the first aspect of this invention a method of making a microelectrode comprising a layer of electrically insulating material having an array of apertures formed therein and electrically conducting material visible through the apertures, is characterized in that the apertures are formed by photo-ablation. Suitably the layer is a sheet of flexible plastics material (suitably a polyester or other polymer film) and the apertures are formed by photo-ablation. A particularly preferred form of electrode made by the method of this invention is a microdisc array electrode in which the apertures are of the same size and shape and are distributed over the sheet in a regular array. In the field of microdisc electrodes the sheet can be of a thickness in the range 2 microns to 500 microns and the apertures are suitably of diameter (or transverse dimension if not circular) of between 5 microns and 100 microns. A hexagonal array of 10 micron diameter apertures with edge/edge separations of 100 microns between the apertures in the array has been found to be one convenient arrangement offering many useful commercial applications.

An alternative method of making the electrode involves supporting a layer of electrode material on a substrate, laying a thin polymer film onto the electrode material (e.g. by vapor polymerization) and then drilling apertures by photo-ablation through the polymer film. The layer of electrode material is conveniently thick-film printed (to any desired pattern) on the substrate. This alternative method has a particular advantage when the electrode material includes carbon, since one photo-ablation used to form the apertures can vitrify one carbon in the areas of electrode material exposed by the photo-ablation.

As well as microdisc arrays the invention extends to microband arrays, a microband array electrode comprising a set of spaced-apart slot-shaped apertures exposing narrow strips (e.g. parallel strips) of a common electrode material.

The formation of the array of apertures by a photo-ablation technique has proved to be particularly convenient and typically involves phonographically creating spaced-apart ablatable areas on the sheet interspersed by more resistant non-ablatable regions, and then removing the sheet material only over the ablatable areas using a high power source of radiation (e.g. from an excimer laser). Using photo-ablation, means that an exceedingly accurate array of apertures of any required size can be produced using well established techniques.

The conducting material is suitably a thixotropic paste based on carbon or metallic particles (e.g. platinum or gold) applied sufficiently thickly so that where the paste is applied to a pre-drilled sheet of plastics material each aperture formed in the non-conducting sheet is substantially filled with conducting particles.

A pre-drilled coated sheet can be bonded, conducting side down, on a substrate of sufficient thickness to give the required rigidity to the sandwich thus produced. The alternative thick film method which drills apertures through to the electrode material already has a suitable support substrate. The substrate can be of electrically conducting or non-conducting material, and can incorporate suitable electrical conductors for applying potentials to and/or leading currents to/from the one or more conducting areas exposed in the apertures.

From the above, it wilt be appreciated that the fabrication method proposed in this first aspect of the invention is essentially a three dimensional thick film process. The procedure circumvents all the past difficulties including the aforementioned, and is based on principles of photo-machining of polymer films by laser photo-ablation to produce matrices of well defined aperture size, distribution, density and geometry. The process can fabricate array patterns in support matrices of thickness 2 µm to 500 µm, and the apertures can be filled with the required conducting particles. The filled sheet can then be mounted by encapsulation on an inert substrate e.g. by a heat sealing process.

A microelectrode made by the method of the invention represents a further aspect of this invention. Initial trials have suggested that such electrodes have useful applications in electroanalysis, high resolution electrochemistry, pathogen testing techniques, antibody or enzyme reactions, and bioelectrochemical assay methods.

The following list details the important characteristics of an electrode made by the method of the invention which underline its use in electroanalysis and application to chemical sensors. It should be appreciated that the method of fabrication here discussed is uniquely controllable in terms of device specification and this has not been found to be true for earlier attempts at fabrication.

1. Uniformity of electrode shapes within an array, size may range from 5 µm to 50 µm in diameter. A reproducible manufacturing method produces identical array electrodes and is essential for reliable analytical application. The small aperture size produces an amperometric signal with improved analytical properties such as detectability, sensitivity and precision even in the presence of dissolved oxygen in the analyte.

2. Variable array size, from a few apertures (say six) to many thousands, The number of apertures within the array will depend on application: cutters amplification increases linearly wish one number of isolated electrodes.
3. Arrays may be patterned: e.g. hexagonal, square etc.
4. The spacing between conducting areas can be varied at will. The ability to set the aperture separation is a very advantageous feature. For example, the separation can be made very small (a few microns) for the monitoring of catalytic current.
5. Arrays of electrodes can be made from different conducting materials (e.g. platinum, gold, carbon etc.).
6. The composition of electrode material can be varied (e.g. ligands and complexing agents can be incorporated in the conducting material to add chemical selectivity to an electroanalysis to be performed with the electrode array).
7. Apertures or groups of apertures within an array can be individually addressed to a set electric potential and therefore the electrode array could be used in multicomponent determination simultaneously.
8. The electrode design is ideally suited to chemical immobilization of reactants (enzyme or antibody) onto the insulating area by covalent bonding hence allowing direct application to biosensor and biochemical assay technology.

A particularly promising application involves the use of an electrode made by the method of this invention for redox species analysis using voltammetry.

Accurate determination of redox species such as pesticides or heavy metals in water is important to the monitoring and control of environmental pollution. The type of information required for comprehensive environment studies not only includes a single sampled measurement of a specific redox species (e.g. metal) at a given place and time, but should include extensive distribution and fluctuation data on major pollutants in order to ascertain origin.

The techniques presently employed by consultant analysts for the determination of heavy metals in water samples include the laboratory based techniques. Atomic Spectroscopy (Absorption and Emission) and Polarography (Pulse and Derivative). These conventional analytical methods are by nature timely and consequently expensive, relying on sampling procedures of a given water supply.

This invention also relates to an analytical method and device which need not be laboratory bound. In one embodiment, the device is a multi-heavy metal ion detector directed essentially at in-the-field measurement which may be used as a portable hand-held device or form part of a remote sensing network.

An analytical method based on this aspect of the invention is electrochemically based and relies on the properties of a microelectrode according to this invention.

According to this aspect of the invention an assay method for a target redox species analysis in a liquid carrier comprises moistening an absorbent medium containing a dry reactant for the species with the liquid carrier, the absorbent medium being sandwiched between two electrodes, one of which is a microelectrode according to this invention, the moistening process being monitored by measuring the conductance between the two electrodes and the concentration of the target redox species being determined by measuring the current flowing between the two electrodes when applying a varying potential therebetween.

Suitably a programmed voltage scan ramp or step formed) is used for the concentration measurement.

The target redox species could be, inter alia, a drug, a bioproduct or a heavy metal ion.

According to a further aspect of the analytical method aspect of the invention an assay method for a trace redox species analysis in a liquid carrier comprises moistening an absorbent medium containing a dry reactant for the species with the liquid carrier, the absorbent medium being sandwiched between two electrodes, one of which is a microelectrode according to this invention, applying a first potential across the electrodes to cause any species drawn into the medium and reacted with the reactant therein to migrate ions onto the conductive areas of the microelectrode, applying a second potential of opposite polarity across the electrodes to strip the said ions from the microelectrode and determining the nature of the "stripped" ion from a knowledge of the redox potential required to effect stripping.

A particularly useful application of the assay method of this invention for trace redox species is in the determination of which heavy metal ions are present in a sample of water, the dry reactant in the absorbent medium being a mercury salt. The method of analysis in this case is an adaption of anodic stripping voltammetry.

In its equipment aspect the invention comprises an assay unit which includes a pad of dry absorbent material incorporating the required dry form redox reagent sandwiched between a microelectrode according to this invention and a counter electrode, the sandwich being mounted on a support means that includes a contact to at least one of the electrodes.

Suitably the support means is a non-conducting (e.g. glass) place having two contacts, one leading to each of the different electrodes. In the case of an assay device for heavy metal detection, the redox reagent can be a mercury salt and where testing on waters with very low electrical conductivity is in mind, a readily ionisable salt (such as sodium chloride).

An assay device in accordance with this aspect of the invention can be used as a disposable component which is connected to (e.g. plugged into) a suitable potentiostat. A fully portable testing equipment is available in this manner, with testing simply requiring a wetting of the absorbent pad of a fresh device and subsequent application of the appropriate potentials to the electrodes using the potentiostat to carry out the required Voltammetry or Anodic Stripping Voltammetry.

BRIEF DESCRIPTION OF DRAWINGS

The various aspects of this invention will now be further described, by way of example, with reference to the accompanying drawings, in which.

DESCRIPTION OF PREFERRED EMBODIMENTS

Figure 1:
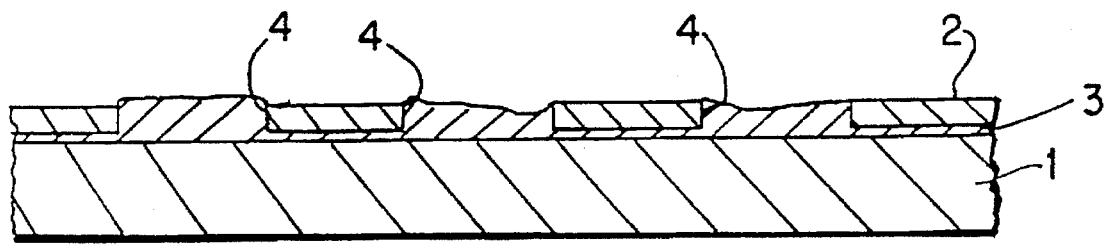
FIG. 1 is a much enlarged sectional view of part of a microdisc array electrode according to the invention.
Figure 2:
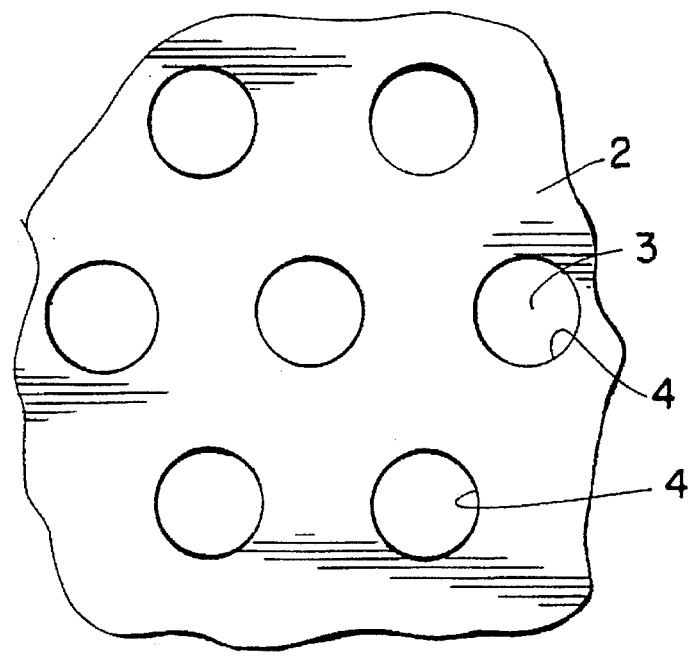
FIG. 2 is a plan view from above of the part shown in FIG. 1.

The microdisc array electrode partially shown in FIGS. 1 and 2 comprises a substrate 1 on which a perforated sheet 2 of non-conducting material coated on one side with a layer 3 of conducting material is applied.

The perforations are regularly spaced equally sized apertures 4 drilled by photo-ablation and forming an array over the entire effective area of the microdisc array electrode.

In a typical case the substrate 1 would be a sheet of polyvinylchloride of a thickness of 500 microns, the sheet 2 a polyester sheet of a thickness of 100 microns and the layer 3 a cured carbon paste of a cured thickness of 500 microns. The array shown in FIG. 2 has circular discs of 10 micron diameter in a 100 micron spaced hexagon pattern. Other geometries such as those leading to microband electrodes are also envisaged. Since each aperture is filled with the conducting paste, each filled aperture forms a conducting area surrounded by a non-conducting region. All exposed conducting areas (or discs) can be connected to the same layer 3 but it will be appreciated that where end uses require different potentials to be applied to different discs or different groups of discs, the layer 3 can be appropriately divided and connected to its own supply lead. The supply lead has not been shown in FIGS. 1 and 2 but such a lead can be seen at 11 in FIG. 5.

Figure 3:
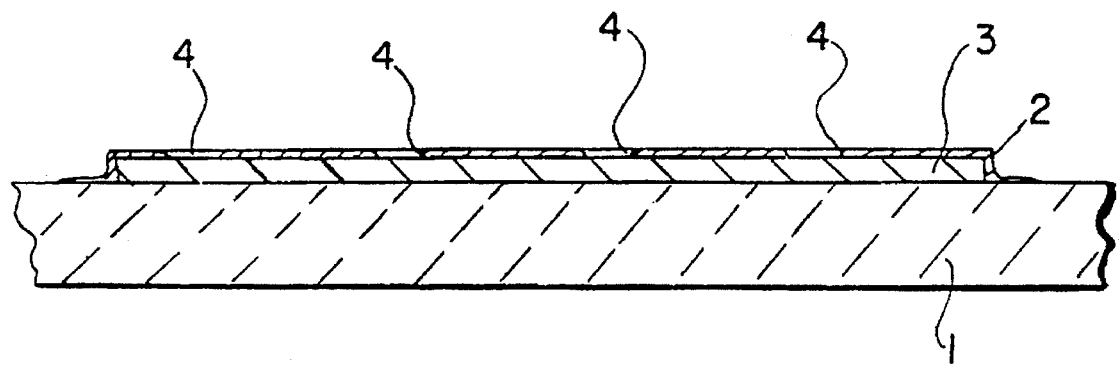
FIG. 3 is a much enlarged sectional side view of part of a microband array electrode according to the invention.
Figure 4:
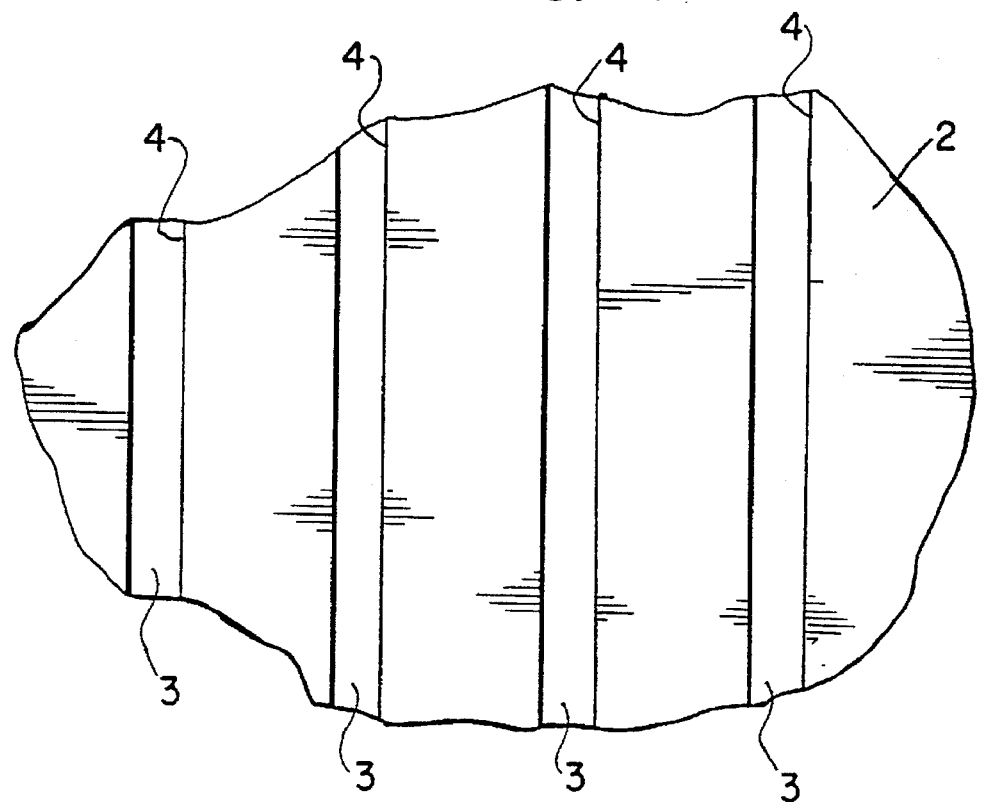
FIG. 4 is a plan view from above of the part shown in FIG. 3.

FIGS. 3 and 4 correspond to FIGS. 1 and 2 but show a microband array electrode the apertures 4 now being narrow slits. The micro-array electrode shown in FIG. 3 was made by thick-film printing conducting electrode material 3 onto an electrically insulating substrate 1 in the required pattern. A layer 2 of polymer film is then vapor polymerized over the printed material 3 and subsequently drilled using laser photo-ablation to produce the apertures 4. With carbon in the material 3 vitrified carbon is formed in the apertures 4 giving the electrode high durability and good electrical properties.

Figure 5:
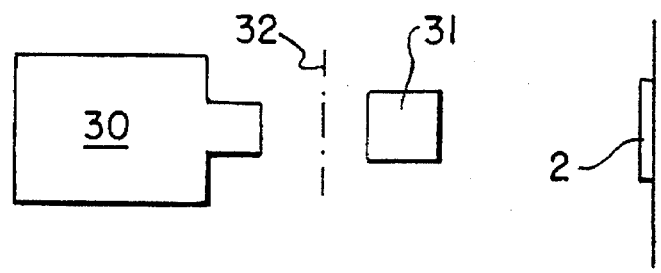
FIG. 5 is a schematic view of laser equipment for forming an array of apertures in a component of a microelectrode.

Photo-ablation of the required aperture pattern is schematically illustrated in FIG. 5 where 30 indicates a high power laser source (e.g. a Lambda Physik LPX 2051 unit), 31 a reducing lens and 2 the plastics film requiring to be drilled. The film 2 can have an apertured mask printed thereon whereby only the film exposed through the apertures in the mask is available for ablation or a mask 32 (e.g. of metal) can be located in the optical path anywhere between the laser source 31 and the film 2. A metal mask contacting the film 2 can also be used.

The minimum size of the apertures 4 that can be produced in a plastics film are expected to be 1 to 2 microns but they can be as large as desired.

The film 2 could be poly-para-xylylene (Parylene N) or other CH materials (such as polystyrene or polyethylene for example).

As examples of suitable laser sources may be mentioned a krF laser (wavelength 248 nm) of fluence in the range 0.2 to 0.4 J/cm$^2$ and (depending on the polymer film 2 being used) ArF (wavelength 193 nm) and XeCl (wavelength 308 nm; lasers of fluences in the range 0.1 to 1.0 J/cm$^2$.

For contact imaging using a metal mask 32 in contact with a Parylene N film of 2 microns thickness, a krF laser of 300 mJ output (a Questek 2440 unit) can be used generating a fluence at the mask of 0.3 J/cm$^2$ over an area of 1 cm$^2$. Using 25 shots of the source 30, an array of 15 micron diameter apertures 4 on 100 micron hole centers was accurately formed in the film 2.

For projection imaging, a metal mask 32 with an array Of 45 micron diameter holes on 300 micron hole centers was located in the beam from a 600 mJ KrF laser and projected down onto a 2 micron thick Parylene N film with a three times reduction of image in the lens 31. The fluence at the mask was 0.044 J/cm$^2$ and at the film it was 0.4 J/cm$^2$. Again 25 shots of the source 30 were required to drill the accurate array of apertures 4 in the film 2.

Figure 6:
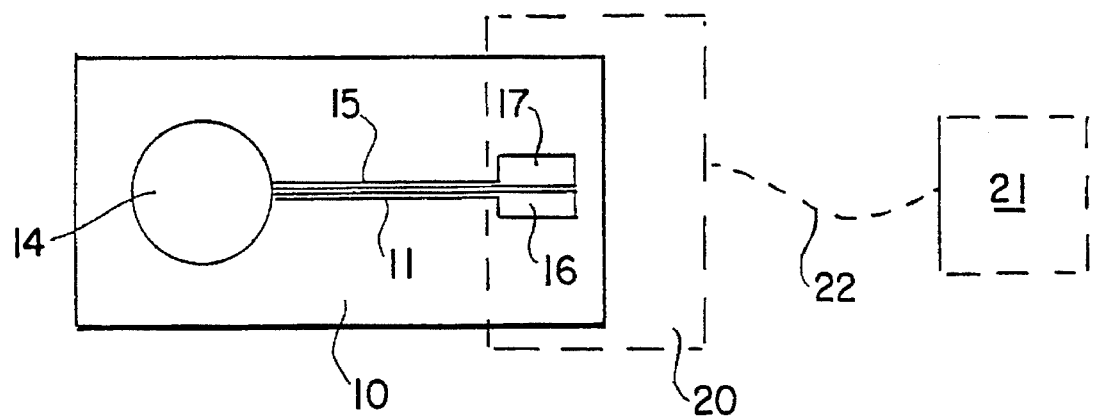
FIG. 6 is a side elevational view of an assay device accordance with a further aspect of the invention.
Figure 7:
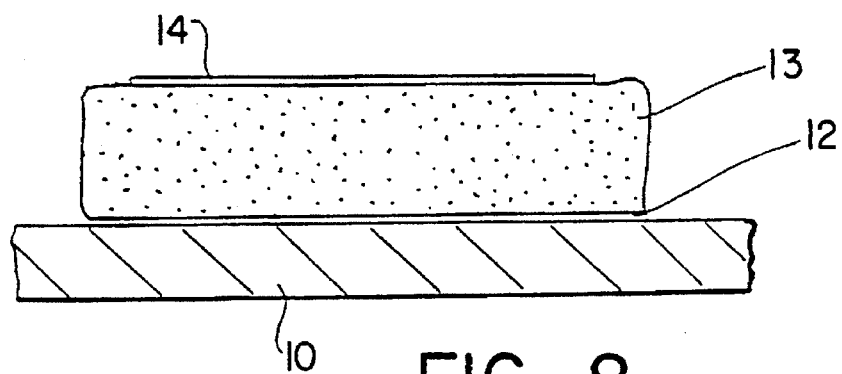
FIG. 7 is a schematic sectional view through part of the device of FIG. 6 with the vertical scale exaggerated for ease of viewing.

The device shown in FIGS. 6 and 7 comprises a rectangular substrate 10 of non-conducting material on which a microelectrode 12 has been provided. Adhered over the electrode 12 is a pad 13 of absorbent material and overlying the pad 13 is a counter electrode 14. The electrode 14 can be applied by printing and will have an area larger than the sum of the apertures of the electrode 13. Conducting leads 11 and 15 connect contact areas 16 and 17 to the two electrodes 12 and 14.

Conveniently, the areas 16 and 17 are positioned so that slipping the substrate 10 into holder (shown dotted at 20) which is connected to an electronic unit 21 by a cable 22, automatically places the device in circuit with the electronic equipment in the unit 21. The unit 21 can comprise a miniatured microprocessor with control potentiostat incorporating a sensitive micrometer.

For testing for the presence of heavy metals (e.g. Pb, Cd, Fe, Zn) in water, the pad 13 will include some particles of common salt and mercurous chloride (say 10% w/w of NaCl and 5% w/w of $Hg_2Cl_2$) or other dried reactants necessary to provide conductivity and oxidized mercury for an electroplating operation. The micro-conducting areas of the electrode 12 will be carbon and the electrode 14 will be of silver/silver chloride. Dipping the pad 13 into a sample of the water to be tested, will draw water into the pad 13 by capillarity action where it will dissolve the salt and redox reagent forming a conductive solution between the electrodes 12 and 14.

For voltammetric analysis, current is passed with electrode 12 as working electrode and electrode 14 as a controlled voltage secondary electrode. The electrochemical reaction on electrode 12, i.e. oxidation or reduction of the target redox species is followed by classical microelectrode electroanalytical methodology.

For stripping analysis, current is passed with electrode 14 as anode to plate mercury and any heavy metal present onto the micro-conductive areas of the electrode 12. Plating current is maintained by hemispherical mass transport inherent to the micro-array geometry for long enough (typically 2 or 3 minutes) to plate a detectable amount of the heavy metal onto the conducting areas.

By virtue of the fact that the microelectrodes are cheap enough to be disposed of after a single use, "memory" problems, such as can occur with laboratory-based equipment, will be avoided since after use for one analysis, the electrode will be discarded.

Figure 8:
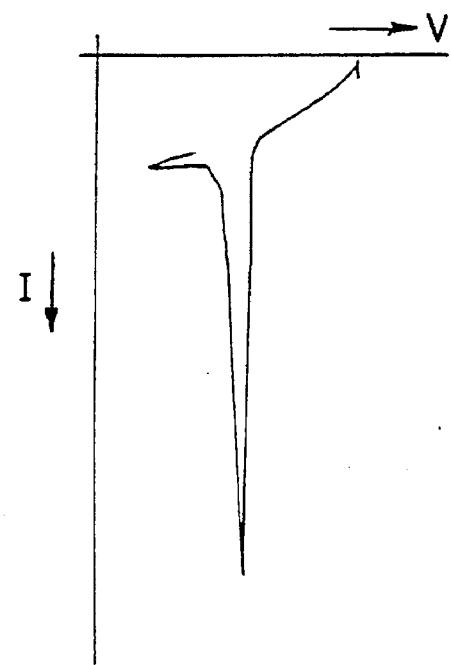
FIG. 8 is a graph showing the applied potential for a trace element detected with a device such as that shown in FIGS. 6 and 7 by stripping analysis.

The polarity of the applied potential is now reversed so that electrode 12 serves as anode are the polarity is increased as a plot is taken of current against voltage. One example of such a plot is shown in FIG. 8 which shows the stripping of leap cations from mercury coated microconductive areas.

It will be appreciated, therefore, that the invention makes possible an assay device which comes in two sections; a sensing unit consisting of a disposable or reusable film cartridge driven by a pocket size computerized potentiostat which comprises the control and signal handling unit. The output of the instrument is a current which is proportional to the concentration of the trace metal ion at a potential specific to the ion itself.

The electroanalysis method described hereabove can be easily adapted to enzyme chemistry or/and immunochemistry for use as a biosensor. Indeed, enzymes or/and antibodies can be covalently immobilized on the perforated polymer sheet 2 in FIG. 1 and electron carrier species often called mediators can be detected on the microelectrode array in a very efficient manner due to the close proximity between the electrode and the immobilized species leading to feedback diffusion enhancement.

It should be stressed that the sensitivity and accuracy of the method and apparatus described herein, are at least comparable to the equivalent laboratory-based methods and equipment.

We claim:

1. A method of analyzing trace metals comprising the steps of:
   (a) providing a plurality of thick-film printed electrodes on a substrate;
   (b) electrolytically depositing a metal film upon at least one of the plurality of thick-film printed electrodes; and
   (c) analyzing a sample for heavy metal content by using electrochemical stripping analysis with the plurality of electrodes.

2. A method as defined in claim 1, wherein step (a) further comprises providing a reference electrode.

3. A method as defined in claim 2, wherein said reference electrode is an Ag/AgCl electrode.

4. A method as defined in claim 1, wherein said plurality of electrodes includes at least one thick-film printed carbon electrode.

5. A method as defined in claim 1, wherein said analyzing is voltammetry.

6. A method as defined in claim 5, wherein said voltammetry is anodic stripping voltammetry.

7. A method as defined in claim 1, further comprising preconcentrating a heavy metal on an electrode.

8. A method as defined in claim 1, wherein said sample comprises water.

9. A method as defined in claim 1, wherein said electrolytically deposited metal comprises mercury.

10. A method as defined in claim 1, wherein said thick-film printed electrodes are directly printed on said substrate.

11. An apparatus for heavy metal trace testing comprising:
    a plurality of thick-film printed electrodes on a substrate;
    a metal film electrodepositor which electrodeposits a metal film on at least one of said electrodes; and
    an electrochemical stripping analyzer which analyzes a sample for heavy metal content with said electrodes.

12. An apparatus as defined in claim 11, further comprising at least one reference electrode.

13. An apparatus as defined in claim 12, wherein said reference electrode is an Ag/AgCl electrode.

14. An apparatus as defined in claim 11, wherein said plurality of electrodes includes at least one thick-film printed carbon electrode.

15. An apparatus as defined in claim 11, wherein said analyzer is a voltammetry analyzer.

16. An apparatus as defined in claim 15, wherein said analyzer is an anionic stripping voltammetry analyzer.

17. An apparatus as defined in claim 11, wherein said metal film electrodepositor is adapted to preconcentrate a heavy metal on said electrode.

18. An apparatus as defined in claim 11, wherein said sample comprises water.

19. An apparatus as defined in claim 11, wherein said metal film comprises mercury.

20. An apparatus as defined in claim 11, wherein said thick-film electrodes are printed on said substrate.

21. A method of analyzing trace metals comprising the steps of:
    (a) providing a plurality of electrodes upon a plastic substrate;
    (b) electrolytically depositing a metal film upon at least one of the plurality of electrodes; and
    (c) analyzing a sample for heavy metal content by using electrochemical stripping analysis with the plurality of electrodes.

22. A method as defined in claim 21, wherein step (a) further comprises providing a reference electrode.

23. A method as defined in claim 22, wherein said reference electrode is an Ag/AgCl electrode.

24. A method as defined in claim 21, wherein said plurality of electrodes includes at least one carbon electrode.

25. A method as defined in claim 21, wherein said analyzing is performed by voltammetry.

26. A method as defined in claim 25, wherein said voltammetry is anodic stripping voltammetry.

27. A method as defined in claim 21, further comprising preconcentrating a heavy metal on an electrode.

28. A method as defined in claim 21, wherein said sample comprises water.

29. A method as defined in claim 21, wherein said electrolytically deposited metal comprises mercury.

30. An apparatus for heavy metal testing comprising:
    a plurality of electrodes upon a plastic substrate;
    a metal film electrodepositor which deposits a metal film on said electrodes; and
    an electrochemical stripping analyzer which analyzes a sample for heavy metal content with said electrodes.

31. An apparatus as defined in claim 30, further comprising at least one reference electrode.

32. An apparatus as defined in claim 31, wherein said reference electrode is an Ag/AgCl electrode.

33. An apparatus as defined in claim 30, wherein said plurality of electrodes includes at least one carbon electrode.

34. An apparatus as defined in claim 30, wherein said analyzer is a voltammetry analyzer.

35. An apparatus as defined in claim 34, wherein said analyzer is an anionic stripping voltammetry analyzer.

36. An apparatus as defined in claim 30, wherein said metal film electrodepositor is adapted to preconcentrate a heavy metal on said electrode.

37. An apparatus as defined in claim 30, wherein said sample comprises water.

38. An apparatus as defined in claim 30, wherein said metal film comprises mercury.

39. A method of analyzing trace metals comprising the steps of:
    (a) providing a plurality of thick-film printed electrodes on a plastic substrate;
    (b) electrolytically depositing a metal film upon at least one of the plurality of thick-film printed electrodes; and
    (c) analyzing a sample for heavy metal content by using electrochemical stripping analysis with the plurality of electrodes.

40. A method as defined in claim 39, wherein step (a) further comprises providing a reference electrode.

41. A method as defined in claim 40, wherein said reference electrode is an Ag/AgCl electrode.

42. A method as defined in claim 39, wherein said plurality of electrodes includes at least one thick-film printed carbon electrode.

43. A method as defined in claim 39, wherein said analyzing is voltammetry.

44. A method as defined in claim 43, wherein said voltammetry is anodic stripping voltammetry.

45. A method as defined in claim 39, further comprising preconcentrating a heavy metal on an electrode.

46. A method as defined in claim 39, wherein said sample comprises water.

47. A method as defined in claim 39, wherein said electrolytically deposited metal comprises mercury.

48. A method as defined in claim 39, wherein said thick-film electrodes are directly printed on said substrate.

49. An apparatus for heavy metal testing comprising:
- a plurality of thick-film printed electrodes on a plastic substrate;
- a metal film electrodepositor which electrodeposits a metal film on at least one of said thick-film electrodes; and
- an electrochemical stripping analyzer which analyzes a sample for heavy metal content with said electrodes.

50. An apparatus as defined in claim 49, further comprising at least one reference electrode.

51. An apparatus as defined in claim 50, wherein said reference electrode is an Ag/AgCl electrode.

52. An apparatus as defined in claim 49, wherein said plurality of electrodes includes at least one thick-film printed carbon electrode.

53. An apparatus as defined in claim 49, wherein said analyzer is a voltammetry analyzer.

54. An apparatus as defined in claim 53, wherein said analyzer is an anionic stripping voltammetry analyzer.

55. An apparatus as defined in claim 49, wherein said metal film electrodepositor is adapted to preconcentrate a heavy metal on said electrode.

56. An apparatus as defined in claim 49, wherein said sample comprises water.

57. An apparatus as defined in claim 49, wherein said metal film comprises mercury.

58. An apparatus as defined in claim 49, wherein said thick-film electrodes are directly printed on said substrate.

59. A method of analyzing trace metals comprising the steps of:
- (a) providing a plurality of electrodes screen-printed on a substrate;
- (c) electrolytically depositing a metal film upon at least one of the plurality of screen-printed electrodes; and
- (c) analyzing a sample for heavy metal content by using electrochemical stripping analysis with the plurality of electrodes.

60. The method of claim 59 wherein the step of providing a plurality of screen-printed electrodes further comprises the step of providing at least one reference electrode.

61. The method of claim 60 wherein the step of providing at least one reference electrode further comprises the step of providing a screen-printed Ag/AgCl electrode.

62. The method of claim 59 wherein the step of providing a plurality of screen-printed electrodes further comprises the step of providing at least one screen-printed carbon electrode.

63. The method of claim 59 wherein the step of analyzing a sample for heavy metal content comprises the step of performing anodic stripping voltammetry on the sample.

64. The method of claim 59 further comprising the step of preconcentrating the heavy metal upon an electrode.

65. The method of claim 64 wherein the step of preconcentrating the heavy metal comprises the step of causing adsorptive accumulation of at least one heavy metal upon said metal film.

66. The method of claim 59 wherein the step of electrolytically depositing a metal film comprises the step of electrolytically depositing mercury.

67. The method of claim 59 wherein the step of electrolytically depositing a metal film comprises the step of electrolytically depositing a member selected from the group consisting of platinum, silver, and gold.

68. The method of claim 59 wherein the step of analyzing a sample for heavy metal content further comprises the step of analyzing a sample of liquid food.

69. The method of claim 59 wherein the step of providing a plurality of electrodes further comprises providing a plastic substrate.

70. Apparatus for heavy metal trace testing comprising:
- means for providing a plurality of electrodes screen-printed on a substrate;
- means for electrolytically depositing a metal film upon at least one of said plurality of screen-printed electrodes; and
- means for analyzing a sample for heavy metal content by electrochemical stripping analysis with said plurality of electrodes.

71. The apparatus of claim 70 wherein said means for providing a plurality of screen-printed electrodes further comprises means for providing at least one reference electrode.

72. The apparatus of claim 71 wherein said means for providing at least one reference electrode further comprises means for providing a screen-printed Ag/AgCl electrode.

73. The apparatus of claim 70 wherein said means for providing a plurality of screen-printed electrodes further comprises means for providing at least one screen-printed carbon electrode.

74. The apparatus of claim 70 wherein said means for analyzing a sample for heavy metal content comprises means for performing anodic stripping voltammetry on the sample.

75. The apparatus of claim 70 further comprising means for preconcentrating said heavy metal upon an electrode.

76. The apparatus of claim 75 wherein said means for preconcentrating said heavy metal comprises means for causing adsorptive accumulation of at least one heavy metal upon said metal film.

77. The apparatus of claim 70 wherein said metal film comprises mercury.

78. The apparatus of claim 70 wherein said metal film comprises a member selected from the group consisting of platinum, silver, and gold.

79. The apparatus of claim 70 wherein said means for analyzing a sample for heavy metal content further comprises means for analyzing a sample of liquid food.

80. The apparatus of claim 70 wherein said substrate comprises plastic.

81. A method of analyzing trace metals comprising the steps of:
- (a) providing a plurality of printed electrodes on a substrate;
- (b) electrolytically depositing a metal film upon at least one of the plurality of printed electrodes; and
- (c) analyzing a sample for heavy metal content by using electrochemical stripping analysis with the plurality of electrodes.

82. A method as defined in claim 81, wherein step (a) further comprises providing a reference electrode.

83. A method as defined in claim 82, wherein said reference electrode comprises an Ag/AgCl electrode.

84. A method as defined in claim 81, wherein said plurality of electrodes includes at least one printed carbon electrode.

85. A method as defined in claim 81, wherein said analyzing comprises voltammetry.

86. A method as defined in claim 85, wherein said voltammetry comprises anodic stripping voltammetry.

87. A method as defined in claim 81, further comprising preconcentrating a heavy metal on an electrode.

88. A method as defined in claim 81, wherein said sample comprises water.

89. A method as defined in claim 81, wherein said electrolytically deposited metal comprises mercury.

90. A method as defined in claim 81, wherein said printed electrodes are printed on said substrate.

91. An apparatus for heavy metal trace testing comprising:
   a plurality of printed electrodes on a substrate;
   a metal film electrodepositor adapted to electrodeposit a metal film on at least one of said electrodes; and
   an electrochemical stripping analyzer adapted to analyze a sample for heavy metal content with said electrodes.

92. An apparatus as defined in claim 91, further comprising at least one reference electrode.

93. An apparatus as defined in claim 92, wherein said reference electrode comprises an Ag/AgCl electrode.

94. An apparatus as defined in claim 91, wherein said plurality of electrodes includes at least one printed carbon electrode.

95. An apparatus as defined in claim 91, wherein said analyzer comprises a voltammetry analyzer.

96. An apparatus as defined in claim 95, wherein said analyzer comprises an anionic stripping voltammetry analyzer.

97. An apparatus as defined in claim 91, wherein said metal film electrodepositor is adapted to preconcentrate a heavy metal on said electrode.

98. An apparatus as defined in claim 91, wherein said sample comprises water.

99. An apparatus as defined in claim 91, wherein said metal film comprises mercury.

100. An apparatus as defined in claim 91, wherein said electrodes are printed on said substrate.

101. A method of analyzing trace metals comprising the steps of:
   (a) providing a plurality of printed electrodes on a plastic substrate;
   (b) electrolytically depositing a metal film upon at least one of the plurality of printed electrodes; and
   (c) analyzing a sample for heavy metal content by using electrochemical stripping analysis with the plurality of electrodes.

102. A method as defined in claim 101, wherein step (a) further comprises providing a reference electrode.

103. A method as defined in claim 102, wherein said reference electrode comprises an Ag/AgCl electrode.

104. A method as defined in claim 101, wherein said plurality of electrodes includes at least one printed carbon electrode.

105. A method as defined in claim 101, wherein said analyzing comprises voltammetry.

106. A method as defined in claim 105, wherein said voltammetry comprises anodic stripping voltammetry.

107. A method as defined in claim 101, further comprising preconcentrating a heavy metal on an electrode.

108. A method as defined in claim 101, wherein said sample comprises water.

109. A method as defined in claim 101, wherein said electrolytically deposited metal comprises mercury.

110. A method as defined in claim 101, wherein said electrodes are printed on said substrate.

111. An apparatus for heavy metal testing comprising:
   a plurality of printed electrodes on a plastic substrate;
   a metal film electrodepositor adapted to electrodeposit a metal film on at least one of said electrodes; and
   an electrochemical stripping analyzer adapted to analyze a sample for heavy metal content with said electrodes.

112. An apparatus as defined in claim 111, further comprising at least one reference electrode.

113. An apparatus as defined in claim 112, wherein said reference electrode comprises an Ag/AgCl electrode.

114. An apparatus as defined in claim 111, wherein said plurality of electrodes includes at least one printed carbon electrode.

115. An apparatus as defined in claim 111, wherein said analyzer comprises a voltammetry analyzer.

116. An apparatus as defined in claim 115, wherein said analyzer comprises an anionic stripping voltammetry analyzer.

117. An apparatus as defined in claim 111, wherein said metal film electrodepositor is adapted to preconcentrate a heavy metal on said electrode.

118. An apparatus as defined in claim 111, wherein said sample comprises water.

119. An apparatus as defined in claim 111, wherein said metal film comprises mercury.

120. An apparatus as defined in claim 111, wherein said electrodes are printed on said substrate.

121. A method of analyzing trace metals comprising the steps of:
   a) providing a plurality of flat printed electrodes;
   b) coating at least one of the plurality of flat printed electrodes with a metal film; and
   c) analyzing a sample for heavy metal content with the plurality of electrodes;
   wherein said step of providing a plurality of flat printed electrodes further comprises the step of providing at least one flat screen-printed Ag/AgCl reference electrode, and at least one flat screen-printed carbon electrode.

122. The method of claim 121 wherein the step of analyzing a sample for heavy metal content further comprises the step of voltammetrically analyzing the sample.

123. The method of claim 121 wherein the coating step comprises coating with mercury.

124. The method of claim 123 wherein the coating step is performed electrolytically.

125. An apparatus for heavy metal trace testing comprising:
   means for providing a plurality of flat printed electrodes;
   means for coating at least one of said plurality of flat printed electrodes with a metal film; and
   means for analyzing a sample for heavy metal content with said plurality of electrodes;
   wherein said means for providing at least one of said plurality of flat printed electrodes comprises means for providing at least one flat screen-printed Ag/AgCl reference electrode, and at least one flat screen-printed carbon electrode.

126. The apparatus of claim 125 wherein said means for analyzing a sample for heavy metal content further comprises means for voltammetrically analyzing said sample.

127. The apparatus of claim 125 wherein said means for coating comprises means for coating with mercury.

128. The apparatus of claim 127 wherein said means for coating comprises means for coating electrolytically.

* * * * *